United States Patent
Vogl et al.

(10) Patent No.: US 10,800,728 B2
(45) Date of Patent: Oct. 13, 2020

(54) METHOD FOR PRODUCING DIALKYLDICARBONATES USING TERTIARY AMINES AS CATALYSTS

(71) Applicants: LANXESS Deutschland GmbH, Cologne (DE); Erasmus Vogl, Bergisch-Gladbach (DE); Christoph Hofmann, Cologne (DE)

(72) Inventors: Erasmus Vogl, Bergisch-Gladbach (DE); Christoph Hofmann, Cologne (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 16/330,169

(22) PCT Filed: Sep. 2, 2016

(86) PCT No.: PCT/EP2016/070701
§ 371 (c)(1),
(2) Date: Mar. 4, 2019

(87) PCT Pub. No.: WO2018/041360
PCT Pub. Date: Mar. 8, 2018

(65) Prior Publication Data
US 2019/0185407 A1 Jun. 20, 2019

(51) Int. Cl.
*C07C 68/02* (2006.01)
*C07C 69/96* (2006.01)

(52) U.S. Cl.
CPC .............. *C07C 68/02* (2013.01); *C07C 69/96* (2013.01)

(58) Field of Classification Search
CPC ................................ C07C 68/02; C07C 69/96
See application file for complete search history.

(56) References Cited

U.S. PATENT DOCUMENTS

| 3,240,796 | A  | 3/1966  | Thoma et al.   |
| 3,326,958 | A  | 6/1967  | Curtins et al. |
| 5,231,211 | A  | 7/1993  | Tang           |
| 7,420,076 | B2 | 9/2008  | Prinz et al.   |
| 7,629,485 | B2 | 12/2009 | Miyake         |
| 8,039,659 | B2 | 10/2011 | Duex et al.    |

FOREIGN PATENT DOCUMENTS

SU 1267746 2/2000

OTHER PUBLICATIONS

International Search Report from corresponding International Application No. PCT/EP20161070701, dated May 22, 2017, two pages.

*Primary Examiner* — Alicia L Otton
(74) *Attorney, Agent, or Firm* — Nicanor A. Kohncke

(57) ABSTRACT

The present invention relates to a method for preparing dialkyl dicarbonates from the corresponding alkyl chloroformates using specific tertiary amines as catalysts.

18 Claims, No Drawings

METHOD FOR PRODUCING DIALKYLDICARBONATES USING TERTIARY AMINES AS CATALYSTS

The present invention relates to a method for preparing dialkyl dicarbonates from the corresponding alkyl chloroformates using specific tertiary amines as catalysts.

Dialkyl dicarbonates are used, e.g., as catalysts for the oxidation of sterically challenging amines, as constituents of electrolyte fluids or as constituents of antimicrobial reagents. Dialkyl dicarbonates are also referred to in the literature as dialkyl pyrocarbonates.

It is known from DE 1 210 853 B to react carbonyl halides with organic hydroxyl compounds or alkali metal or alkaline earth metal salts thereof, and organic, water-immiscible solvents and at least equivalent amounts of alkali metal or alkaline earth metal hydroxides or carbonates in a biphasic system, and using catalytic amounts of tertiary amines or quaternization products thereof, wherein the amines or quaternization products thereof used are those bearing at least one ω-hydroxyalkyl, ω-hydroxyalkyl ether or ω-hydroxyalkyl polyether group bonded to nitrogen.

DE-A 1 418 849 furthermore describes tertiary amines as particularly suitable catalysts for the preparation of acid derivatives, the tertiary nitrogen atoms of which are not sterically hindered, excluding tertiary amines bearing the same ω-hydroxyalkyl, ω-hydroxyalkyl ether or ω-hydroxyalkyl polyether group as substituents on the nitrogen. In addition to triethylamine and tri-n-butylamine, amines are therefore used here which bear at least one methyl group on the nitrogen, such as N-methyl-di-n-stearylamine. However, these catalysts have the disadvantage, inter alia, that they catalyze not only the formation but also the decomposition of the product, which results in a decreased yield. In addition, some of these catalysts are toxic, are poorly degraded in wastewater and are difficult to separate from the reaction mixture owing to their decomposition during the reaction.

Known from EP 1747185 A is a method for preparing dialkyl dicarbonates from alkyl haloformates by reaction with alkali metal or alkaline earth metal hydroxides or carbonates, in which long-chain tertiary $C_6$-$C_{25}$-alkylamines are used. These catalysts are also toxic, poorly degrade in wastewater and therefore represent an ecological burden.

There is therefore a need for a preparation method which affords the target product in high yield and in which the catalysts can be more readily removed.

Surprisingly, it has been found that dialkyl dicarbonates can be obtained particularly advantageously from alkyl haloformates by reaction with alkali metal or alkaline earth metal hydroxides or carbonates, when specific long-chain tertiary amines of the formula (I) are used as catalyst. These are characterized by high catalytic activity, without causing decomposition of the end product and can be easily removed from the product, for example by distillation. They are also less toxic than comparable phase transfer catalysts and are more readily degraded in the context of wastewater treatment.

Accordingly, the present invention relates to a method for preparing dialkyl dicarbonates by reacting the corresponding alkyl haloformates with alkali metal or alkaline earth metal hydroxides and/or carbonates in the presence of water-immiscible organic solvents and in the presence of a catalyst, characterized in that the catalyst used is at least one tertiary amine of the formula (I)

$$NR^1R^2R^3 \quad (I)$$

where
$R^1$=straight-chain or branched $C_1$-$C_6$-alkyl,
$R^2$=straight-chain or branched $C_{16}$-$C_{22}$-alkyl and
$R^3$=—$[CH_2$—$R^4$—$O]_n$—$[CH_2$—$R^4]$—OH, where n=0 to 12 and $R^4$=—$[CH_2$—$CH_2]$—, —$[CH(CH_3)]$— or —$CH_2$—.

When carrying out the method according to the invention, preference is given to using tertiary amines of the formula (I) as catalyst, where
$R^1$=methyl, ethyl, propyl or butyl,
$R^2$=straight-chain or branched $C_{17}$-$C_{20}$-alkyl and
$R^3$=—$[CH_2$—$(CH(CH_3))$—$O]_n$—$[CH_2$—$(CH(CH_3))]$—OH, —$[CH_2$—$CH_2$—$CH_2$—$O]_n$—$[CH_2$—$CH_2$—$CH_2]$—OH or —$[CH_2$—$CH_2$—$O]_n$—$[CH_2$—$CH_2]$—OH where n=6 to 12.

Particular preference is given to using the catalyst where $R^1$=methyl, $R^2$=straight-chain $C_{18}$-alkyl and $R^3$=—$[CH_2$—$CH(CH_3)$—$O]_n$—$[CH_2$—$CH(CH_3)]$—OH where n=8.

In one embodiment of the method according to the invention, an amine of the general formula (I) is used as catalyst in which $R^2$ in each case signifies straight-chain or branched hexadecanyl, heptadecanyl, octadecanyl, nonadecanyl, eicosanyl, icosanyl, heneicosanyl or dodoconyl. Preferably, $R^2$=straight-chain octadecanyl.

When carrying out the method according to the invention, any desired mixtures of the catalysts may also be used. In a preferred embodiment of the method according to the invention, the catalysts used are mixtures of two or more tertiary amines of the formula (I), in which $R^3$ is —$[CH_2$—$(CH(CH_3))$—$O]_n$—$[CH_2$—$(CH(CH_3))]$—OH and n has various values in the range from 8 to 11, particularly preferably=8, 9, 10 or 11.

In a further preferred embodiment, the catalysts used are mixtures of compounds of the formula (I) which comprise various radicals $R^2$ that are straight-chain or branched $C_{16}$-, $C_{17}$-, $C_{18}$-, $C_{19}$-, $C_{20}$- or $C_{21}$-alkyl.

In a further preferred embodiment, it is possible to use mixtures of the compounds of the formula (I) as catalysts, in which the radicals $R^1$, $R^2$ and $R^3$ in the context of the above disclosure are combined in any manner.

The dialkylamines typically used for preparing the catalysts, such as N-methylstearylamine, are commercially available. Their preparation methods are furthermore known to those skilled in the art. The preparation of the specific tertiary amines of the formula (I) is also known, for example, from DE 1210853 B and is typically carried out by reacting the dialkylamines with propylene oxide or ethylene oxide in the presence of alkali metal hydroxides.

Preferably, the method according to the invention serves to prepare dialkyl dicarbonates of the formula (II)

where
$R^5$ is straight-chain or branched $C_1$-$C_{20}$-alkyl,
by reacting alkyl haloformates of the formula (III)

where

Hal is halogen, preferably F, Cl, Br, I, especially chlorine, and $R^5$ is straight-chain or branched $C_1$-$C_{20}$-alkyl, characterized in that the reaction is carried out in the presence of at least one tertiary amine of the formula (I) as catalyst $$NR^1R^2R^3 \qquad (I)$$

where $R^1$=straight-chain or branched $C_1$-$C_6$-alkyl.
$R^2$=straight-chain or branched $C_{16}$-$C_{22}$-alkyl and
$R^3$=—[CH$_2$—R$^4$—O]$_n$—[CH$_2$—R$^4$]—OH, where n=0 to 12 and $R^4$=—[CH$_2$—CH$_2$]—, —[CH(CH$_3$)]— or —CH$_2$—.

In the formulae (II) and (III), $R^5$ is preferably straight-chain or branched $C_1$-$C_8$-alkyl, particularly preferably a radical —CH—R$^6$R$^7$, in which $R^6$ and $R^7$ are each independently H or straight-chain or branched $C_1$-$C_7$-alkyl. In particular, $R^5$ is methyl, ethyl, n-propyl, isopropyl, n-butyl or isobutyl. Particularly preferably, $R^5$ is methyl, so that dimethyl dicarbonate is obtained as compound of the formula (II).

Useful alkali metal or alkaline earth metal hydroxides or carbonates are, for example, LiOH, NaOH, KOH, LiCO$_3$, Na$_2$CO$_3$, K$_2$CO$_3$. Preference is given to using alkali metal hydroxides such as sodium and potassium hydroxide, which are preferably used in the form of aqueous solutions. For example, 1 to 50% by weight aqueous alkali metal hydroxide solutions can be used. Preference is given to 5 to 35% by weight solutions, particularly preferably 10 to 25% by weight solutions. The alkali metal or alkaline earth metal hydroxides or carbonates can be used, for example, in amounts of 80 to 120 mol %, based on haloformic acid ester used. This amount is preferably in the range from 90 to 110 mol %, particularly preferably in the range from 95 to 105 mol %.

Useful water-immiscible organic solvents are for example aliphatic and aromatic hydrocarbons, halogenated hydrocarbons, water-immiscible ethers or esters and also dialkyl carbonates. Preference is given to cyclohexane, toluene, xylene, methylene chloride and diethyl ether, especially toluene and methylene chloride.

The water-immiscible organic solvent can be used, for example, in amounts from 20 to 90% by weight, preferably from 30 to 80% by weight, particularly preferably from 40 to 70% by weight, based on the haloformic acid ester of the formula (I).

The catalyst of the formula (I) is generally used in an amount from 0.001 to 0.5 mol %, preferably from 0.005 to 0.05 mol %, based on haloformic acid ester.

The method according to the invention can be carried out in a pressure range from 1 to 10 bar, preferably from 1 to 1.5 bar.

The reaction temperature can be, for example, between −10° C. and the boiling temperature (at standard pressure) of the haloformic acid ester used. It is preferably in the range from 0 to 50° C.

It is advantageous while carrying out the method according to the invention to provide thorough mixing, for example by using stirrers, baffles or circulation pumps.

The method according to the invention can be carried out both in batchwise mode and continuously. In the batchwise mode of operation, the reaction is preferably carried out in a stirred tank. The reaction in this case is generally terminated after 10 minutes to 3 hours, depending on the size of the batch and the available cooling power.

The method according to the invention is preferably carried out continuously using a stirred tank, a stirred tank cascade or a tubular reactor. In this case, the mean residence time in the reactor is generally between 1 and 60 minutes, preferably between 6 and 45 minutes and particularly preferably between 10 and 20 minutes.

After carrying out the method according to the invention, if applicable after cooling, the reaction mixture separates into two phases. The organic phase comprises, in addition to the solvent, the dialkyl dicarbonate produced and possibly low amounts of unreacted haloformic acid ester and the catalyst. The aqueous phase comprises the inorganic salts formed in addition to water.

The reaction product can be obtained from the organic phase by multi-stage distillation in high purity. The catalyst can be removed in this case as high boiler and can be reused (recyclization) as catalyst in the method according to the invention, optionally after purification.

It is a particular and surprising advantage of the method according to the invention that the catalyst conveniently does not catalyze the decomposition of the dialkyl dicarbonates after the reaction and can therefore be separated off by distillation, whereby the isolated yield of end product is higher in comparison to conventional methods. The catalysts used are considerably superior to the currently known phase transfer catalysts, also with respect to separation and recovery. The superior degradability of catalysts of the formula (I), optionally present in the wastewater, is also a decisive advantage in the context of wastewater treatment compared to the catalysts of the prior art.

What is claimed is:

1. A method for preparing dialkyl dicarbonates, the method comprising contacting one or more alkyl haloformates with at least one alkali metal hydroxide, alkaline earth metal hydroxide and/or carbonate in the presence of at least one water-immiscible organic solvent and in the presence of a catalyst, wherein the catalyst comprises at least one tertiary amine of the formula (I)

$$NR^1R^2R^3 \qquad (I)$$

where $R^1$=straight-chain or branched $C_1$-$C_6$-alkyl,
$R^2$=straight-chain or branched $C_{16}$-$C_{22}$-alkyl, and
$R^3$=—[CH$_2$—R$^4$—O]$_n$—[CH$_2$—R$^4$]—OH,
where n=0 to 12 and $R^4$=—[CH$_2$—CH$_2$]—, —[CH(CH$_3$)]—, or —CH$_2$—.

2. The method as claimed in claim 1, wherein the at least one tertiary amine of the formula (I) comprises at least one tertiary alkylamine of the formula (I) where:

$R^1$=methyl, ethyl, propyl or butyl,
$R^2$=$C_{17}$-$C_{20}$-alkyl, and
$R^3$=—[CH$_2$—CH(CH$_3$)—O]$_n$—[CH$_2$—CH(CH$_3$)]—OH or —[CH$_2$—CH$_2$—CH$_2$—O]$_n$—[CH$_2$—CH$_2$—CH$_2$]—OH where n=6 to 10.

3. The method as claimed in claim 2, wherein:

$R^1$=methyl,
$R^2$=straight-chain $C_{18}$-alkyl, and
$R^3$=—[CH$_2$—CH(CH$_3$)—O]$_n$—[CH$_2$—CH(CH$_3$)]—OH where n=8.

4. The method as claimed in claim 3, wherein:

the at least one alkali metal hydroxide, alkaline earth metal hydroxide and/or carbonate are in the form of aqueous solutions;

the at least one water-immiscible organic solvent is selected from the group consisting of aliphatic and aromatic hydrocarbons, chlorinated hydrocarbons, dialkyl carbonates, and water-immiscible ethers and esters;

the contacting is done in the presence of 0.001 to 0.5 mol % of the tertiary amines of the formula (I), based on the alkyl haloformates, and at a temperature between −10° C. and the boiling temperature (at standard pressure) of the alkyl haloformates;

the contacting comprises a continuous operation; and upon completion, the dialkyl dicarbonates are in an organic phase, and the method further comprises separating the dialkyl dicarbonates by phase separation and subsequent multi-stage distillation of the organic phase.

5. The method as claimed in claim 1, wherein:
the catalyst comprises a mixture of two or more different tertiary amines of the formula (I), and
$R^3$ is $-[CH_2-(CH(CH_3))-O]_n-[CH_2-(CH(CH_3))]-OH$ where n=8, 9, 10 or 11.

6. The method as claimed in claim 1, wherein the catalyst comprises a mixture of the tertiary amines of the formula (I) comprising various radicals $R^2$ that are straight-chain or branched $C_{16}$-, $C_{17}$-, $C_{18}$-, $C_{10}$-, $C_{20}$- or $C_{21}$-alkyl.

7. The method as claimed in claim 1, wherein:
the dialkyl dicarbonates comprises dialkyl dicarbonates of the formula (II)

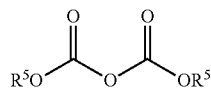

where
$R^5$ is straight-chain or branched $C_1$-$C_{20}$-alkyl, and the alkyl haloformates comprise alkyl haloformates of the formula (III)

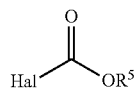

where
Hal is F, Cl, Br, or I and
$R^5$ is straight-chain or branched $C_1$-$C_{20}$-alkyl.

8. The method as claimed in claim 1, wherein the at least one alkali metal hydroxide, alkaline earth metal hydroxide and/or carbonate are in the form of aqueous solutions.

9. The method as claimed in claim 1, wherein the at least one water-immiscible organic solvent is selected from the group consisting of aliphatic and aromatic hydrocarbons, chlorinated hydrocarbons, dialkyl carbonates, and water-immiscible ethers and esters.

10. The method as claimed in claim 1, wherein the contacting is done in the presence of 0.001 to 0.5 mol % of the tertiary amines of the formula (I), based on the alkyl haloformates.

11. The method as claimed in claim 1, wherein the contacting is carried out at a temperature between −10° C. and the boiling temperature (at standard pressure) of the alkyl haloformates.

12. The method as claimed in claim 1, wherein the contacting comprises a continuous operation.

13. The method as claimed in claim 1, further comprising, after termination of the reaction, separating off the dialkyl dicarbonates by phase separation and subsequent multi-stage distillation of the organic phase.

14. A method for preparing dialkyl dicarbonates of the formula (II)

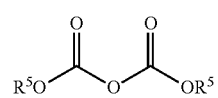

where $R^5$ is straight-chain or branched $C_1$-$C_{20}$-alkyl, the method comprising contacting alkyl haloformates of the formula (III)

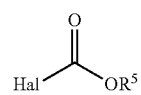

where
Hal is halogen,
with at least one alkali metal hydroxide, alkaline earth metal hydroxide and/or carbonate in the presence of at least one water-immiscible organic solvent and in the presence of a catalyst, wherein the catalyst comprises at least one tertiary amine of the formula (I)

$NR^1R^2R^3$ (I)

where
$R^1$=methyl, ethyl, propyl or butyl,
$R^2$=$C_{17}$-$C_{20}$-alkyl, and
$R^3$=$-[CH_2-CH(CH_3)-O]_n-[CH_2-CH(CH_3)]-OH$ or $-[CH_2-CH_2-CH_2-O]_n-[CH_2-CH_2-CH_2]-OH$ where n=6 to 10.

15. The method according to claim 14, wherein $R^5$ is straight-chain or branched $C_1$-$C_8$-alkyl.

16. The method according to claim 14, wherein $R^5$ is methyl, ethyl, n-propyl, isopropyl, n-butyl or isobutyl.

17. The method according to claim 16, wherein:
$R^1$=methyl, ethyl, propyl or butyl,
$R^2$=$C_{17}$-$C_{20}$-alkyl, and
$R^3$=$-[CH_2-CH(CH_3)-O]_n-[CH_2-CH(CH_3)]-OH$ or $-[CH_2-CH_2-CH_2-O]_n-[CH_2-CH_2-CH_2]-OH$ where n=6 to 10.

18. The method according to claim 17, wherein:
Hal=chlorine,
$R^5$=methyl,
$R^1$=methyl,
$R^2$=straight-chain $C_{15}$-alkyl,
$R^3$=$-[CH_2-CH(CH_3)-O]_n-[CH_2-CH(CH_3)]-OH$ where n=8; and
the at least one alkali metal hydroxide, alkaline earth metal hydroxide and/or carbonate comprises at least one of LiOH, NaOH, KOH, $LiCO_3$, $Na_2CO_3$, and $K_2CO_3$.

* * * * *